United States Patent [19]

Schäl

[11] Patent Number: 4,923,598
[45] Date of Patent: May 8, 1990

[54] APPARATUS FOR THE TREATMENT OF BLOOD IN PARTICULAR FOR HEMODIALYSIS AND HEMOFILTRATION

[75] Inventor: Wilfried Schäl, Bad Homburg, Fed. Rep. of Germany

[73] Assignee: Fresenius AG, Fed. Rep. of Germany

[21] Appl. No.: 209,678

[22] Filed: Jun. 21, 1988

[30] Foreign Application Priority Data

Jun. 23, 1987 [DE] Fed. Rep. of Germany ....... 3720665

[51] Int. Cl.$^5$ ...................... B01D 13/00; B01D 35/00
[52] U.S. Cl. ......................... 210/87; 210/90; 210/137; 210/143; 210/321.65; 210/929; 604/5
[58] Field of Search ................... 210/87, 90, 137, 143, 210/321.65, 321.71, 929; 604/4, 5

[56] References Cited

U.S. PATENT DOCUMENTS

| | | | |
|---|---|---|---|
| 3,946,731 | 3/1976 | Lichtenstein | 210/929 |
| 4,021,341 | 5/1977 | Cosentino et al. | 210/321.65 |
| 4,145,925 | 3/1979 | Stasz et al. | 128/662.01 |
| 4,147,059 | 4/1979 | Fathauer | 128/662.01 |
| 4,509,528 | 4/1985 | Sahota | 128/691 |
| 4,542,644 | 9/1985 | Claytor et al. | 73/599 |
| 4,596,549 | 6/1986 | Minami | 210/140 |
| 4,711,715 | 12/1987 | Polaschegg | 210/137 |
| 4,718,890 | 1/1988 | Peabody | 604/65 |
| 4,735,727 | 4/1988 | Heitmeier et al. | 210/87 |
| 4,747,822 | 5/1988 | Peabody | 604/29 |

Primary Examiner—W. Gary Jones
Attorney, Agent, or Firm—Townsend and Townsend

[57] ABSTRACT

The apparatus for hemodialysis and hemofiltration comprises an extracorporeal blood circuit comprising a dialyzer and/or filter arrangement. For determining the fluid withdrawal per unit time and the total amount of fluid withdrawn flow sensors in conjunction with an evaluating unit are inserted into the blood circuit upstream and downstream of the dialyzer or filter arrangement. The flow measurement is by the ultrasonic Doppler principle and for obtaining high accuracy the sensors comprise measuring inserts belonging to the blood tubing system and having special means for defined coupling-in and coupling-out and precise conduction of the ultrasonic waves. Apart from the measurement, means are provided for regulating the net fluid withdrawal.

22 Claims, 5 Drawing Sheets

APPARATUS FOR THE TREATMENT OF BLOOD IN PARTICULAR FOR HEMODIALYSIS AND HEMOFILTRATION

The invention relates to an apparatus for the treatment of blood, in particular hemodialysis and hemofiltration, which is used to treat the blood of a patient in an artificially created extracorporeal blood cycle by dialysis and/or filtration, possibly combined with a supply of infusion solutions into the blood circulation, in such a manner that the greatest possible normalization of the composition of the blood plasma is achieved. Apparatuses of this type are able to replace the function of the kidneys and are also known under the name "artificial kidney".

For the medical success and for compatibility of such a treatment it is of course of great importance to exactly determine the net withdrawal of fluid from the blood and regulate this withdrawal by appropriate adjustment of the operating parameters by hand or automatically. Various systems are known for this purpose.

Proceeding from the consideration that the withdrawal of a predetermined fluid volume per unit time is necessarily linked to a corresponding reduction of the blood volume returned to the patient per unit time, in specification as laid open to inspection DE No. 33 13 421 A1 it is proposed for example in a dialysis apparatus to equip the extracorporeal blood cycle with a differential flow meter and to utilize the information thus obtained in a manner known per se for controlling the fluid withdrawal.

The main problem in the implementation of a measurement of a fluid withdrawal per unit time is however finding flowmeters suitable for measuring the blood flow.

DE No. 33 13 421 A1 has proposed for this purpose employing preferably electromagnetic flowmeters, presumably this means inductive flowmeters, which are to have specifically selected flexible tubes each with two inserted electrodes to which an electromagnetic field is applied to withdraw therefrom a voltage proportional to the difference of the flow rates. Apart from this erroneous interpretation of the function principle this does not solve the problem of how the technical difficulties preventing obtaining an accuracy and operational reliability adequate for the intended purpose can be overcome.

For blood flow measurement by the induction principle it is necessary to bring the flow passage into a magnetic field which is directed transversely of the flow and is as homogeneous as possible so that transversely of the flow direction and transversely of the direction of the magnetic field by means of electrodes disposed oppositely at the flow passage an induced voltage U can be tapped off which is proportional to the magnetic flux density B, the electrode spacing d and the mean flow rate v: $U = B \cdot d \cdot v$. With a circular flow cross-passage as present with blood tubes the mean flow rate v, the blood flow Q (volume per unit time) and the tube internal diameter di are also related in accordance with the relationship $v = 4 \cdot Q/di^2 \cdot \pi$. These two relationships give $U = 4 \cdot B \cdot Q \cdot d/di^2 \cdot \pi$, i.e. to obtain adequate accuracy it is not enough to compensate the two tube diameters di but in addition the values of the magnetic flux density B and the electrode spacing d must be brought into coincidence to the extent of the required accuracy.

A further difficulty when using inductive flowmeters for said purpose results from the fact that the difference of the iduced voltages is extremely small so that when they are processed additional errors occur due to the inevitable disturbing voltages which are several orders of magnitude higher.

The order of magnitude of the induced voltages results from the following estimation: The air gap of the magnetic system must correspond at least to the tube external diameter. This is typically about 6 mm. To obtain an approximately homogeneous magnetic field in the region of the measuring point the cross-sectional area of the air gap must be several times greater than the square of the tube diameter, for example $10 \text{ mm} \cdot 10 \text{ mm} = 100 \text{ mm}^2$. In accordance with the usual dimensioning rules for electromagnets, in such an air gap with an electromagnet still of acceptable size and power (weight of a few 100 g, power a few watts) a magnetic flux density of the order of magnitude of 0.5 mT can be generated. A typical value of the blood flow is $Q = 200$ ml/min. Taking account of a tube internal diameter and an electrode spacing of $di = d = 4$ mm this then gives at one of the flowmeters an induced voltage of only about 50 microvolts. The voltage difference between the two flowmeters is even smaller by a factor of at least 10, i.e. 5 microvolts. It is a difficult technical problem to process with adequate accuracy such a small measurement voltage under the conditions present in a dialysis machine, i.e. in an open system which can be shielded only to a limited extent due to the necessary replaceability of all the parts coming into contact with the blood, and this problem could probably be solved only with an unacceptably high expenditure and with considerable restrictions as regards handling of the apparatus.

Apart from this, in the measurement of flowing blood an inductive flowmeter has the disadvantage that the blood must be brought into contact via electrodes with electrical circuits and that to establish these connections between the replaceable blood tubing system intended to be used once only and the measurement circuits corresponding electrical contact means must be provided and the function thereof would be greatly jeopardized by the operation in an environment which is always moist due to the use of disinfectants, infusion solutions, and the like.

Another method of measuring blood flow is the ultrasonic Doppler technique. This method has fundamentally the advantage that it is indeed a non-invasive measurement and that in particular no electrical connections to the measured medium must be established. In the book "Replacement of Renal Function by Dialysis" (W. Drukker et al., Martinus Nijhoff Publishers, The Hague, 1978), on page 267 this method is considered for monitoring blood flow in hemodialysis; however, it is considered on the whole to be of little practical value with the present state of technical development, although theoretically advantageous on the whole. A more detailed assessment of a commercial device for measuring blood flow by the ultrasonic Doppler technique is to be found in the book "Technical Aspects of Renal Dialysis" (T. H. Frost, Pittman Medical Publications, Tunbridge Wells, 1978). The accuracy of the measuring device is investigated therein under various influences and is rated to be comparable to the air bubble transit time method. This is however of course relatively inaccurate so that on the basis of this assessment as well it was not actually to be expected that with the aid of two flowmeters operating by this principle an adequately accurate determination of the liquid withdrawal in hemodialysis and hemofiltration apparatuses would be possible.

The invention was based on the problem of further developing the apparatus of the type mentioned at the beginning in such a manner that reproduceable measurements of the blood flow can be carried out with increased accuracy.

The invention was also based on the problem of providing a hemodialysis and hemofiltration apparatus having a functionable means practicable under real operating conditions for measuring the fluid withdrawal by difference formation of the output signals of two flowmeters, one of which is inserted into the blood line leading from the patient to the dialyzer or filter arrangement and the second of which is inserted into the blood line leading from the dialyzer or filter arrangement to the patient.

This problem is solved in that the flow sensor comprises a dimensionally stable measuring insert inserted into the blood tubing system and having defined flow cross-section and lateral extensions for the defined coupling-in and coupling-out and conducting of the ultrasonic waves.

The arrangement according to the invention has the advantage that it provides a considerably improved measurement accuracy over the conventional measuring arrangements operating by the ultrasonic Doppler technique. Thus, the measurement error limits for usual flow sensors, which are about 5%, can be considerably reduced by the apparatus according to the invention. Consequently, for example with the apparatus according to the invention a measurement error limit of about 1% and below can be obtained.

According to a preferred embodiment two flowmeters of the type according to the invention are arranged upstream and downstream respectively of a filter unit or dialyzer in the extracorporeal blood cycle. These flowmeters are each connected to an evaluating unit which in accordance with a predetermined computing operation forms a difference value between the respective signals. Since with such a difference formation the usual measuring errors can be filtered out the actual measuring error with the arrangement according to the invention can be reduced to 0.1% and below. The arrangement according to the invention can therefore also be used to determine the slightest changes in the flow rate, for example for setting low ultrafiltration rates in hemodialysis.

The treatment of blood according to the invention includes not only blood purification in the form of hemodialysis or filtration but also any other type of extracorporeal blood treatment in which the blood flow and the blood pressure set are to be monitored and recorded. Thus, the arrangement according to the invention can also be used in heart-lung machines or plasmapheresis centrifuges.

Further properties and advantages of the invention and further developments thereof will be apparent from the following description.

Figure 1:
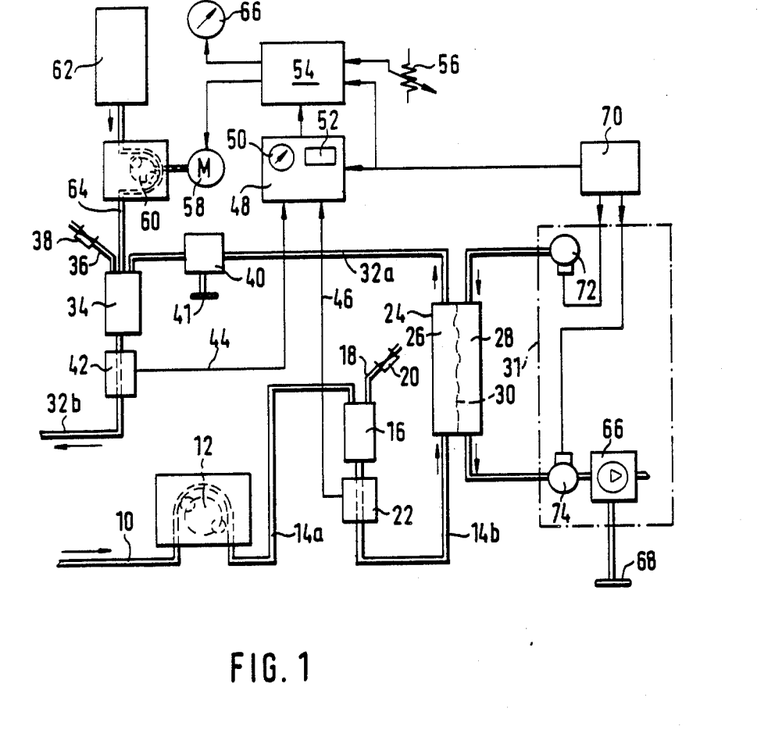
FIG. 1 is a schematic of the fluid circuits of a hemodialysis and hemofiltration apparatus corresponding to the invention.

In FIG. 1 the schematic of the fluid circuits of a hemodialysis and hemofiltration apparatus corresponding to a preferred example of embodiment of the invention is shown. The blood withdrawn from the patient for example via a catheter passes through the conduit 10 to the inlet of the blood pump 12 and is supplied by the latter via the conduit 14a, 14b to the dialyzer or filter arrangement 24. The latter includes a space or chamber 26 traversed by the blood and a space or chamber 28 which is separated therefrom by a semipermeable membrane 30 and provided for the passage of dialysis fluid and/or withdrawal of filtrate, the filtrate (also called ultrafiltrate) passing through the semipermeable membrane 30 from the space 26 to the space 28 under the influence of the pressure difference between the spaces 26 and 28, the so-called transmembrane pressure.

The means for operating the dialyzer or filter arrangement 24, for example for traversing with dialysis solution and/or withdrawal of filtrate, are combined in the operating unit 31. The latter is known in various forms which are all suitable for the present purpose. It may for example consist of a container with dialysis solution and a circulating pump or it may comprise a means of known type for continuous generation of dialysis solution. In pure filtration operation it usually consists of a suction means and a collecting vessel for the extracted filtrate. In the simplest case the space 28 is connected only to a collecting vessel, the filtrate passing through the membrane 30 into the space 28 only under the influence of the blood pressure existing in the space 26 and being collected in the collecting vessel.

The blood passes from the dialyzer or filter arrangement 24 through the conduit 32a to the chamber 34 which in known manner serves inter alia for separation of any air bubbles entrained. From the lower part of the chamber 34 the blood flows through the conduit 32b back to the patient. Inserted into the conduit 32b downstream of the chamber 34 is the discharge-side flow sensor 42, the configuration of which according to the invention will be described below. It is connected via the electrical line 44 to the evaluating unit 48.

In accordance with a preferred development of the invention a chamber 16 and downstream thereof the supply-side flow sensor 22 are also inserted into the line 14a, 14b leading to the dialyzer or filter arrangement. The insertion of the chamber 16 has inter alia the advantage that air which can be sucked into the blood circuit on occurrence of a leak in the region of the conduit 20 and the associated patient connection is separated and thus does not reach the dialyzer or filter arrangement where it could collect, in particular in the capillary dialyzers or filters usually employed today, and clog part of the capillaries or at least interfere with the flow path. This would result in a reduction of the effectiveness and could moreover promote a partial coagulation of the blood in the dialyzer or filter arrangement so that complete flushing back of the blood at the end of the treatment would not be possible. The insertion of the chamber 16 into the conduit 14a, 14b and the arrangement of the flow sensor 22 downstream of the chamber 16 are however also of particular significance to the function and flow measurement. If air passes through the sensor the measurement signal obtained thereby is useless so that the measurement would be mutilated.

The chambers 34 and 16 are equipped with means for removing collected air. In accordance with FIG. 1 for this purpose a flexible tube 36 or 18 can be connected to the upper part of the chamber, said tube normally being closed with a cock or a clamp 38 or 20 respectively. In addition, it is expedient to equip the chambers with means for monitoring the air amount collected, for example with level sensors. These are not shown in FIG. 1. Also not shown is a means for monitoring the pressure in the return blood conduit which is normally connected to the chamber 34.

The two flow sensors 22 and 42 are connected via electrical lines 46 and 44 respectively to the evaluating unit 48. In the latter the signals furnished by the sensors are processed, inter alia for controlling a display means 50 for the net fluid withdrawal rate, i.e. for the amount of fluid which is withdrawn from the patient per unit time, and a display means 52 for the total amount of fluid withdrawn. Details of the function of the evaluating unit will be described below in conjunction with FIG. 7.

A further important addition of the preferred example of embodiment is the control unit 54. On the basis of a comparison between the desired value of the net fluid withdrawal rate preselected at a setting means 56 and the actual value of the net fluid withdrawal rate determined by the evaluating unit 48 said control unit controls the drive motor 58 of the infusion pump 60 in such a manner that the drive speed increases when the actual value of the net fluid withdrawal rate exceeds the desired value. The infusion pump delivers from a supply means, for example a reservoir 62, an infusion solution through the conduit 64 into the chamber 34 where it mixes with the blood conducted back to the patient. The amount of liquid supplied per unit time is also indicated on the display means 66.

For operating the arrangement shown in FIG. 1 at the setting means 56 firstly the desired reference or desired value of the net fluid withdrawal rate is set. As long as the amount of fluid passing per unit time from the blood space 26 through the membrane 30 to the space 28 due to the transmembrane pressure in the dialyzer or filter arrangement is less than the desired value of the net fluid withdrawal rate the infusion pump is stationary corresponding to the properties of the control unit 54 because in this condition the actual value of the net fluid withdrawal rate is less than the desired value. The transmembrane pressure is now increased by increasing the pressure in the space 26 and/or lowering the pressure in the space 28. The pressure increase in the space 26 can be effected by means of a throttle 40 arranged at the conduit 32a and the pressure reduction in the space 28 likewise by setting a corresponding throttle valve or by increasing the suction power of a suction means 66 belonging to the operating unit 31, for example with a pump.

As soon as, due to the increased transmembrane pressure, the amount of fluid passing through the membrane 30 per unit time exceeds the set desired value of the net fluid withdrawal rate, the infusion pump 60 starts operating and due to the characteristics of the control unit 54 the infusion pump 60 supplies per unit time as much infusion solution as is necessary to replace the part of the fluid amount separated out via the membrane 30 per unit time which exceeds the desired value of the net fluid withdrawal rate. Thus, starting from a specific rate of blood supply which is detected by the sensor 22 in the equilibrium condition the control of the drive of the infusion pump 60 causes the latter to supply an amount of solution such that the flow rate of the blood returning to the patient detected by the second sensor 42 differs by the intended difference amount corresponding to the net fluid withdrawal rate preselected at the setting means 56.

The amount of infusion solution supplied per unit time can be read from the display means 66. By observing this display the transmembrane pressure can be adjusted with the aid of the setting means 41 and/or 68 in such a manner that the amount of infusion solution supplied per unit time lies in the desired order of magnitude.

Disturbances in the blood circuit or in the operating unit 31 lead generally to a change in the transmembrane pressure and thus influence the passage of solution through the membrane 30. Due to the properties of the control circuit described this automatically leads to a correction in the form of a corresponding change in the solution supply by the infusion pump 60 and of the value displayed on the display instrument 66. By using a display instrument 66 with adjustable alarm limit contacts, as indicated in FIG. 1, or an equivalent means for limit value monitoring it is thus possible to detect automatically such a disturbance. This has the substantial advantage that the very complex and disturbance-prone pressure measuring devices otherwise usual for detecting such disturbances by monitoring the transmembrane pressure can be dispensed within this system.

In a further development the invention provides a means for automatic periodic calibration of the flow sensors in conjunction with the evaluating unit 48. It includes the calibration control unit 70 and the valves 72 and 74 which are controlled by said unit and which can be closed for the purpose of calibration by the corresponding control signal. Simultaneously, the drive of the infusion pump 60 is stopped. The closure of said valves serves to shut off the space 28 of the dialyzer or filter arrangement 24 so that a further passage of filtrate from the space 26 through the membrane 30 into the space 28 is prevented. Under these conditions an identical flow is obtained in the two flow sensors 22 and 42. If there is a deviation between the two measured values furnished by the flow sensors said deviation is determined in the evaluating unit 48 and stored and used for error correction in the operating time following the calibration. In this manner a zero point correction is achieved with regard to the difference formation between the measurement signals of the flow sensors and thus the main possible disturbing influence eliminated.

Figure 2:
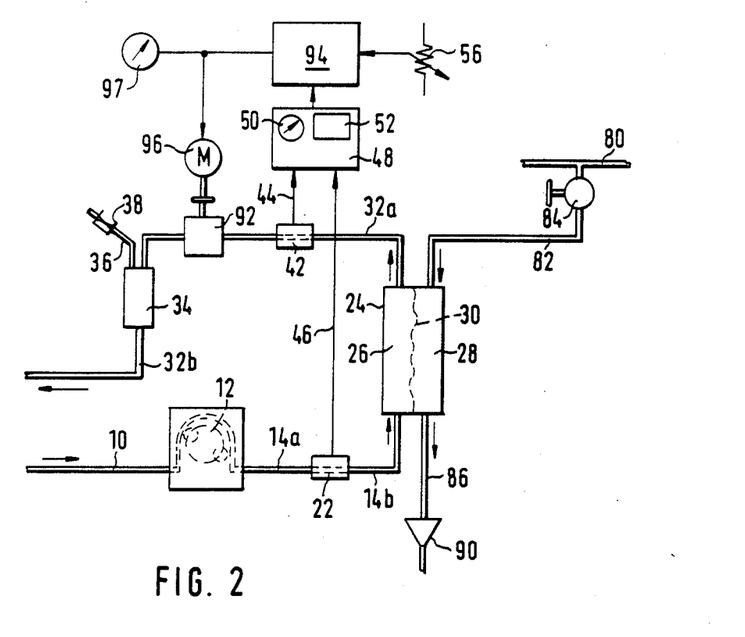
FIG. 2 is a second example of an embodiment in schematic form.

Another embodiment of a hemodialysis and hemofiltration apparatus corresponding to the invention is shown schematically in FIG. 2. For establishing a flow through the space 28 of the dialyzer or filter arrangement said space is connected on the one hand to a distributor conduit 80 of a central supply system for dialysis solution and on the other to a drain 90. The flow is set by a cock 84. In pure filtration operation the cock 84 remains closed.

The extracorporeal blood cycle includes two flow sensors 22 and 42 in the supply conduit 14a, 14b and in the discharge conduit 32a, 32b respectively of the space 26 of the dialyzer or filter arrangement 24. They are connected as in the previous embodiment via electrical lines 44 and 46 to the evaluating unit 48 which comprises a display means 50 for the difference between the signals furnished by the two flow sensors. Due to the arrangement preferred for this embodiment of the flow sensors directly upstream and downstream of the space 26 of the dialyzer and filter arrangement this difference corresponds to the amount of fluid per unit time which passes by filtration from the space 26 through the membrane 30 into the space 28. This amount corresponds at the same time to the amount of fluid which is withdrawn from the patient per unit time. For displaying the total amount of fluid withdrawn up to the particular point of time the evaluating unit 48 comprises a further display means 52.

The amount of fluid passing per unit time from the space 26 through the membrane 30 into the space 28 depends on the pressure difference between the spaces 26 and 28. For setting this pressure difference an adjustable throttle 92 is provided at the outgoing blood conduit. In the simplest case the throttle 92 is set by hand whilst observing the display means 50 so that the desired fluid withdrawal per unit time is achieved.

It is however also possible to adjust the throttle 92 automatically by a control. For this purpose the control unit 94 is used which is connected to the setting means 56 for preselecting the desired value of the amount of fluid withdrawn per unit time. The control unit compares this amount with the actual value determined by the evaluating unit 48 and in accordance with the result of this comparison controls a motor 96 for adjusting the throttle 92.

Figure 3:
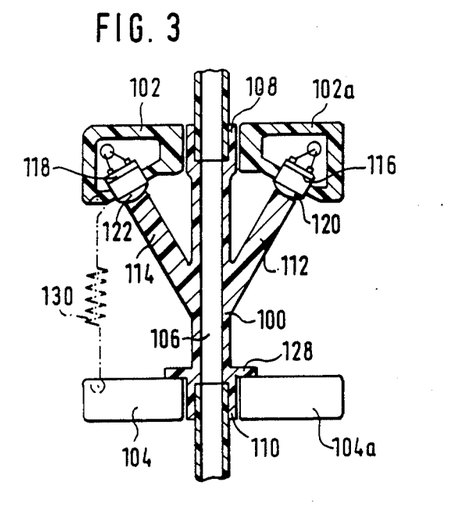
FIG. 3 shows a sensor for the flow measurement.
Figure 4:
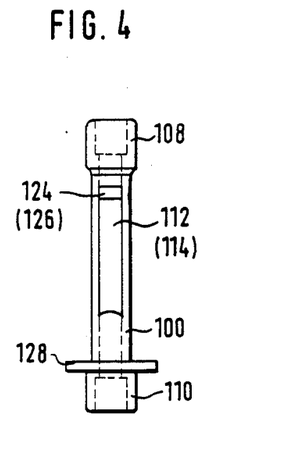
FIG. 4 is a plan view of the measuring insert for the sensor.
Figure 5:
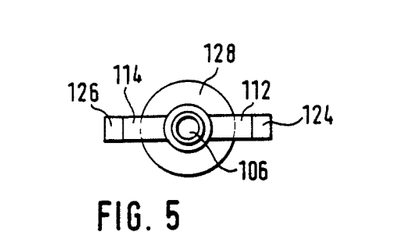
FIG. 5 is a side elevation of the measuring insert for the sensor.

Of essential importance to the invention is the construction of the sensors 22, 42 used for the flow measurement It is illustrated in FIG. 3. The Figure is only a schematic intended to illustrate the main components and their cooperation. The overall arrangement consists essentially of a measuring insert 100 which belongs to the replaceable blood tubing system usually intended to be used only once, and a holder 102, 104 which belongs to the fixed part of the apparatus and in which the measuring insert is secured. The holder preferably consists of two parts which are resiliently connected together for fixing the measuring insert. A side view and a plan view of the measuring insert are illustrated in FIGS. 4 and 5 respectively.

The measuring insert consists of a blood-compatible dimensionally stable and relatively rigid plastic material which can be worked by the usual injection molding processes to give parts of high dimensional accuracy and uniformity. The measuring insert is preferably inserted into the blood tubing system in the factory, for example by the adhesive insertion usual for similar parts of the respective tube portions into the connecting parts 108, 110 of the measuring insert. The measuring insert is sterilized with the tubing system and the entire system, intended to be used only once, is thus transported to the point of use where it is connected up with the remaining apparatus.

The measuring insert comprises a continuous flow passage 106 in continuation of the connected conduit parts. Of particular importance are the two lateral extensions 112, 114 which are directed towards the flow passage and which serve for coupling-in and out the ultrasonic signal and also have the function of conducting the ultrasonic waves, i.e. exactly defining the propagation direction of the coupled-in ultrasonic waves and likewise exactly defining the direction of the maximum intensity of the coupled-out ultrasonic waves. The lateral extensions are at an angle to the longitudinal axis of the flow passage of the order of magnitude for example of 15–50 degrees. To obtain a high sensitivity a relatively small angle is advantageous.

In the upper part 102, 102a of the holder the two ultrasonic transducers for transmitting and receiving the ultrasonic signal are arranged, this being done so that their axes have the same direction as the extensions of the measuring insert serving for the conduction of the ultrasonic waves. They consist essentially each of a transducer element 116, 118 and a coupling piece 120, 122. The coupling pieces are in intimate contact under a certain pressure with the coupling faces 124, 126 of the measuring insert. The transducer elements are preferably discs of a piezoelectric ceramic material which is equipped in usual manner with metal coatings and electrical terminals. The coupling pieces consist, at least in the part which comes into contact with the coupling faces, preferably of a resilient material, for example silicone rubber, so that under the action of the mechanical pressure applied a substantially homogeneously and adequately large contact area is formed which extends as far as possible over the entire coupling area 124, 126. This makes it superfluous to improve the coupling by using contact gels, as is otherwise frequently usual.

The lower part 104, 104a of the holder essentially has the function of fixing the measuring insert 100. For this purpose it is resiliently mounted in a suitable guide with respect to the upper part 102, 102a of the holder as indicated purely schematically in FIG. 3 by a tension spring 130. Of course, the resultant force must act in the axis of symmetry of the arrangement and this is achieved for example by symmetrical arrangement of two springs. The measuring insert comprises for the same purpose a support element 128 which is made for example collar-like and by which the force is transmitted from the lower part of the holder to the measuring insert.

By the coupling-in and out described above and the guiding of the ultrasonic waves the requirements for high accuracy in the measurement of the flow rate are met. Also of considerable significance is that by the configuration of the measuring insert the blood is conducted before and after the actual measuring point over a relatively long distance, amounting to several times the diameter of the flow passage, in a defined rectilinearly extending flow passage so that disturbances of the flow profile due to conduit curvatures are avoided.

Figure 6:
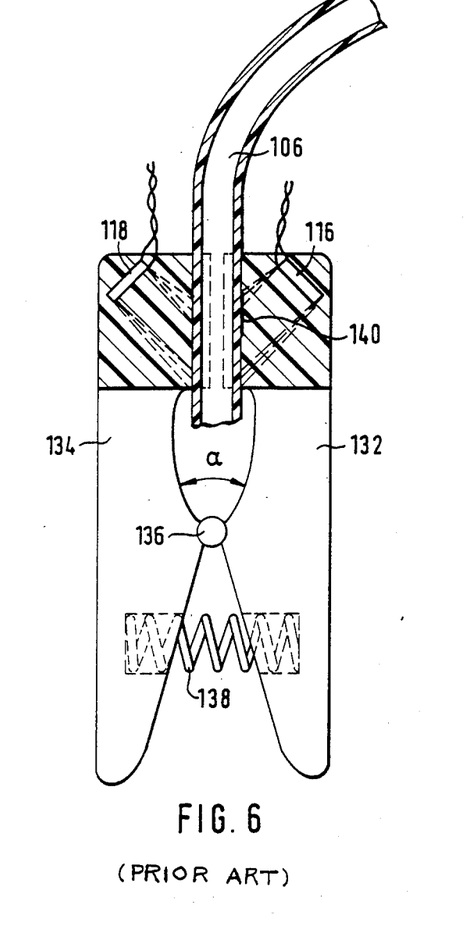
FIG. 6 is a sensor for the flow measurement by the ultrasonic Doppler technique of known construction in schematic illustration, for comparison.

For comparison and clarifying the differences in FIG. 6 the design of the flow sensor of a known blood flowmeter is schematically illustrated, to which the already-mentioned publication in the book "Technical Aspects of Renal Dialysis" (T. H. Frost, Pittman Medical Publications, Tunbridge Wells, 1978) also relates. In this case the sensor is formed like a clip clamped onto the blood tube. For this purpose the two walls of the clamp or clip are connected by a joint 136 and a spring 138. The front part of the cheeks is adapted in its inner contour to the dimensions of the blood tube and encloses the latter. The transducer elements 116, 118 are arranged in the front part of the cheeks and aligned at an angle of about 45 degrees to the blood tube and fixed by embedding in a potting compound.

Such an arrangement has various disadvantages which are avoided in the arrangement described above:

The angle (alpha) between the cheeks varies in dependence upon the tolerances of the tube outer diameter and on pressure changes in the tube and temperature-dependent changes of the elasticity of the tube material. Due to the change of this angle the angle of attack of the transducers in the direction of the flow passage also changes and thus the proportionality factor decisive for the calibration.

Changes in the internal diameter of the tube between the cheeks, for example due to pressure fluctuations or temperature-dependent variation of the elasticity of the tube material in conjunction with the spring force acting, also influence the length of the path covered by the ultrasonic waves in the blood and thus likewise lead to changes in the measurement signal.

The main propagation direction of the ultrasonic waves from the transmitter-side transducer into the flow passage on the one hand and the direction of the maximum sensitivity for the ultrasonic waves reaching the receiving-side transducer from the flow passage on the other is influenced by the transmission conditions at the interface between the inner contour of the cheek and the outer surface of the tube. Non-uniform pressure distribution and/or incomplete area contact, in particular dirt particles or air bubbles (140 in FIG. 6) which may be included in the gel used to improve the coupling, thus also change the proportionality factor decisive for the calibration in an unpredictable manner.

Since they are usually made by an extrusion method the internal cross-section area of the flexible tubes are prone to considerable tolerances. Due to the relationship between flow speed, mean flow rate and cross-sectional area this leads to a corresponding additional measurement uncertainty.

Since the flow passage does not have a predefined direction on both sides of the measuring point changes in the flow profile which lead to corresponding errors arise due to displacement, for example curving, of the tube.

Compared with an inductive flowmeter, in which not only the flow cross-section but also the magnetic flux density and the electrode spacing must be maintained high accuracy, these high demands in the subject of the invention, assuming exact guiding of the ultrasonic waves, are restricted substantially to the accuracy of the flow cross-section and of the stimulation frequency. By making the measuring insert by precision injection molding and using a quartz-controlled generator for the oscillation stimulation both requirements can be met with small expenditure. A further advantage of the flow measurement by the ultrasonic Doppler principle over the inductive flow measurement is due to the fact that the amplitude of the measurement signals plays a secondary part. The measuring effect is based on the contrary to a change in frequency which can be evaluated relatively easily free from error.

Figure 7:
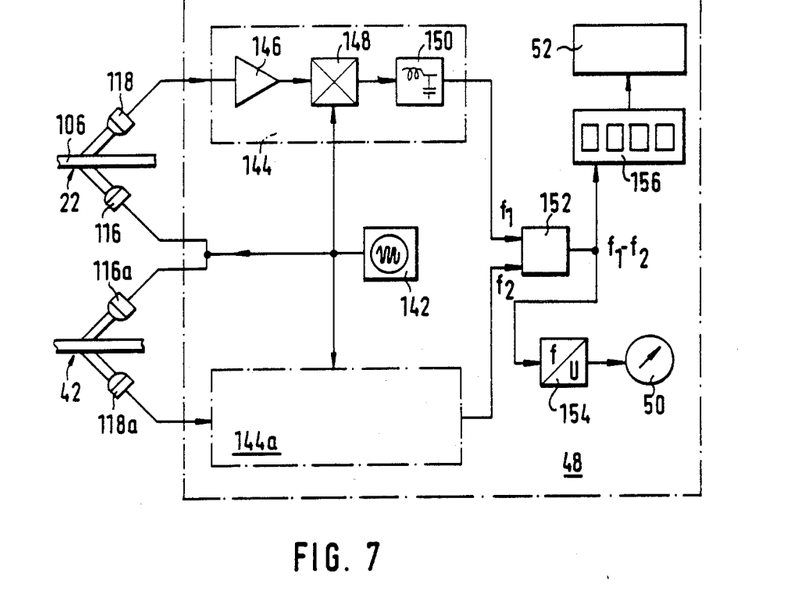
FIG. 7 is a block diagram of a circuit arrangement for the signal processing.

FIG. 7 shows a block diagram of a circuit arrangement of the flow sensors 22 and 42 which corresponds to the evaluating circuit 48 in FIG. 1 and FIG. 2. The transmitter-side ultrasonic transducers 116, 116a are fed jointly by a high-frequency generator 142 with a frequency of the order of magnitude of a few MHz. The signals furnished by the receiver-side ultrasonic transducers 118, 118a contain apart from components of the transmission frequency the actual measurement signal in the form of an oscillation component which due to the Doppler effect has a frequency shift proportional to the flow rate. These signals are processed separately in two identical circuit units 144, 144a. The signal is first brought by the amplifier 146 to an adequate amplitude and supplied to a mixing stage 148 to recover the low-frequency difference frequency f1 or f2 proportional to the flow rate. Said frequency is available at the output of the following low-pass filter 150 separate from the remaining frequency components. In a further circuit unit 152 the difference f1–f2 is finally formed from f1 and f2 and is decisive for the difference of the flows in the two flow sensors and thus for the fluid withdrawal per unit time.

To display this quantity the signal f1–f2 may be converted for example by a frequency-voltage converter 154 to a voltage and the display instrument 50 controlled thereby. To display the total amount of fluid withdrawn the signal f1–f2 is supplied to a counter 156 and the respective count displayed on the display means 52.

I claim:

1. An apparatus for the extracorporeal treatment of blood, comprising:
   an extracorporeal blood circuit which is formed by a blood tubing system;
   means for dialyzing, filtering or both located in said extracorporeal blood circuit;
   a first ultrasonic flow sensor located in said extracorporeal blood circuit upstream of the dialyzing and filtering means, comprising:
      a first dimensionally stable measuring insert inserted into the blood tubing system having a defined flow cross-section and lateral extensions for coupling-in said coupling-out and conducting of ultrasonic waves, each said extension having at one end a coupling face;
      ultrasonic transducers with piezoelectric transducer elements having coupling pieces connected thereto and disposed such that each said coupling piece is in mechanical engagement with a corresponding coupling face;
   a second ultrasonic flow sensor located in said extracorporeal blood circuit downstream of the dialyzing and filter means, comprising:
      a second dimensionally stable measuring insert inserted into the blood tubing system having a defined flow cross-section and lateral extensions for coupling-in and coupling-out and conducting of ultrasonic waves, each said extension having at one end a coupling face;
      second ultrasonic transducers with piezoelectric transducer elements having coupling pieces connected thereto and disposed such that each said coupling piece is in mechanical engagement with a corresponding coupling face;
   evaluating means for performing predetermined evaluating operations based on signals generated by the first and second flow sensors connected to the first and second flow sensors; and
   withdrawal control means for controlling the withdrawal of fluid from the extracorporeal blood circuit via the dialyzer or filter means, based on said evaluating operations.

2. The apparatus according to claim 1, wherein said evaluating means comprising:
   means for determining the difference between the flow rate through said first flow sensor and said second flow sensor; and
   means for displaying from said determining means the amount of fluid withdrawn from a patient per unit time.

3. The apparatus according to claim 1, wherein said evaluating means comprising:
   means for determining the difference between the flow rate through said first flow sensor and said second flow sensor;
   means for forming the time integral of the difference of the flow rates; and
   means for displaying from said integral forming means the total amount of fluid withdrawn from a patient.

4. The apparatus according to claim 1, further comprising:
   infusion control means connected to said blood circuit for controlling the infusion into said blood circuit of an infusion solution; and
   second evaluating means for performing predetermined evaluating operations for automatic control of said infusion control means.

5. The apparatus according to claim 4, further comprising:
   display means connected to said infusion control means for indicating and limit-value monitoring of the supply rate of the infusion solution.

6. The apparatus according to claim 1, wherein said dialyzing and filtering means includes a first chamber through which blood flows and a second chamber through which dialysis fluid or withdrawal of filtrate flows, the first and second chambers separated by a semipermeable membrane across which a transmembrane pressure differential is maintained, said apparatus further comprising:
   pressure control means connected to the evaluating means for automatic setting of the transmembrane pressure.

7. The apparatus according to claim 6, further comprising:
   a drive-motor actuated throttle connected to the pressure control means and located downstream of the filtering and dialyzing means for controlling fluid flow through the blood circuit.

8. The apparatus according to claim 7, further comprising:
   display means connected to said pressure control means for indicating and limit-value monitoring the transmembrane pressure.

9. The apparatus according to claim 8, wherein said display means is adapted to display and limit-value monitor the position of the drive motor actuating the throttle.

10. The apparatus according to claim 1, further comprising:
    automatic periodic calibration means connected to the evaluating means, comprising:
    calibration control means;
    a plurality of valves for isolating the dialyzing and filtering means from the blood circuit controlled by said calibration means;
    said evaluating means for determining the difference of measurement between signals issuing from said first flow sensor and said second flow sensor and for determining therefrom a zero point correction, the evaluating means further comprising:
    means for storing said difference of measurement signals and the zero point correction corresponding to the magnitude of said difference of measurement signals.

11. The apparatus according to claim 1, wherein the longitudinal axes of the lateral extensions of the measuring inserts form an angle in the range 10-60 degrees with the longitudinal axis of the measuring inserts.

12. The apparatus according to claim 1, wherein the longitudinal axes of the lateral extensions of the measuring inserts form an angle of 30 degrees with the longitudinal axis of the measuring inserts.

13. The apparatus according to claim 1, wherein that portion of the each coupling piece in contact with the corresponding coupling face is a rubber-elastic material.

14. The apparatus according to claim 1, wherein each said measuring insert comprises:
    a fixed part for receiving and containing the transducers; and
    an element resiliently mounted with respect to said fixed part for affixing the fixed part to the measuring insert.

15. The apparatus according to claim 1, wherein said evaluating means further includes means for determining the flow rate through said blood circuitry employing the Doppler effect.

16. The apparatus for the extracorporeal treatment of blood, comprising:
    an extracorporeal blood circuit which is formed by a blood tubing system;
    means for dialyzing, filtering or both located in said extracorporeal blood circuit;
    a first ultrasonic flow sensor located in said extracorporeal blood circuit upstream of the dialyzing and filtering means, comprising:
       a first dimensionally stable measuring insert inserted into the blood tubing system having a defined flow cross-section and lateral extensions for coupling-in and coupling-out and conducting of ultrasonic waves, each said extension having at one end a coupling face;
       first ultrasonic transducers with piezoelectric transducer element having coupling pieces connected thereto and disposed such that each said coupling piece is in mechanical engagement with a corresponding coupling face;
    a second ultrasonic flow sensor located in said extracorporeal blood circuit downstream of the dialyzing and filter means, comprising:
       a second dimensionally stable measuring insert inserted into the blood tubing system having a defined flow cross-section and lateral extensions for coupling-in and coupling-out and conducting of ultrasonic waves, each said extension having at one end a coupling face;
       second ultrasonic transducers with piezoelectric transducer elements having coupling pieces connected thereto and disposed such that each said coupling piece is in mechanical engagement with a corresponding coupling face;
    first evaluating means connected to the first and second flow sensors, comprising:
       means for determining the difference between the flow rate through said first flow sensor and said second flow sensor;
       means for forming the time integral of the difference of the flow rates;
    means for displaying from said determining means the amount of fluid withdrawn from a patient per unit time and the total amount of fluid withdrawn from a patient;
    withdrawal control means for controlling the withdrawal of fluid from the extracorporeal blood circuit via the dialyzer or filter means, based on said evaluating operations;

infusion control means connected to said blood circuit for controlling the infusion into said blood circuit of an infusion solution; and second evaluating means for performing predetermined evaluating operations for automatic control of said infusion control means.

17. The apparatus according to claim 16, further comprising:
display means connected to said infusion control means for indicating and limit-value monitoring of the supply rate of the infusion solution.

18. The apparatus according to claim 16, further comprising:
automatic periodic calibration means connected to the evaluating means, comprising:
calibration control means;
a plurality of valves for isolating the dialyzing and filtering means from the blood circuit controlled by said calibration means;
said evaluating means for determining the difference of measurement between signals issuing from the first flow sensor and said second flow sensor and for determining therefrom a zero point correction, the evaluating means further comprising:
means for storing said difference of measurement signals and the zero point correction corresponding to the magnitude of said difference of measurement signals.

19. An apparatus for the extracorporeal treatment of blood, comprising:
an extracorporeal blood circuit which is formed by a blood tubing system;
means for dialyzing, filtering or both located in said extracorporeal blood circuit including a first chamber through which blood flows and a second chamber through which dialysis fluid or withdrawal of filtrate flows, the first and second chambers separated by a semipermeable membrane across which a transmembrane pressure differential is maintained;
a first ultrasonic flow sensor located in said extracorporeal blood circuit upstream of the dialyzing and filtering means, comprising:
a first dimensionally stable measuring insert inserted into the blood tubing system having a defined flow cross-section and lateral extensions for coupling-in and coupling-out and conducting of ultrasonic waves, each said extension having at one end a coupling face;
second ultrasonic transducers with piezoelectric transducer elements having coupling pieces connected thereto and disposed such that each said coupling piece is in mechanical engagement with a corresponding coupling face;
a second ultrasonic flow sensor located in said extracorporeal blood circuit downstream of the dialyzing and filter means, comprising;
a second dimensionally stable measuring insert inserted into the blood tubing system having a defined flow cross-section and lateral extensions for coupling-in and coupling-out and conducting of ultrasonic waves, each said extension having at one end a coupling face;
second ultrasonic transducers with piezoelectric transducer elements having coupling pieces connected thereto and disposed such that each said coupling piece is in mechanical engagement with a corresponding coupling face;
first evaluating means connected to the first and second flow sensors, comprising:
means for determining the difference between the flow rate through said first flow sensor and said second flow sensor;
means for forming the time integral of the difference of the flow rates;
means for displaying from said determining means the amount of fluid withdrawn from a patient per unit time and the total amount of fluid withdrawn from a patient;
withdrawal control means for controlling the withdrawal of fluid from the extracorporeal blood circuit via the dialyzer or filter means, based on said evaluating operations;
pressure control means connected to the first evaluating means for automatic setting of the transmembrane pressure; and
a drive-motor actuated throttle connected to the pressure control means and located downstream of the filtering and dialyzing means for controlling fluid flow through the blood circuit.

20. The apparatus according to claim 19, further comprising:
display means connected to said pressure control means for indicating and limit-value monitoring the transmembrane pressure.

21. The apparatus according to claim 20, wherein said display means is adapted to display and limit-value monitor the position of the drive motor actuating the throttle.

22. The apparatus according to claim 19, further comprising:
automatic periodic calibration means connected to the evaluating means, comprising:
calibration control means;
a plurality of valves for isolating the dialyzing and filtering means from the blood circuit controlled by said calibration means;
said evaluating means for determining the difference of measurement between signals issuing from the first flow sensor and said second flow sensor and for determining therefrom a zero point correction, the evaluating means further comprising:
means for storing said difference of measurement signals and the zero point correction corresponding to the magnitude of said difference of measurement signals.

* * * * *